(12) United States Patent
Schneider

(10) Patent No.: US 7,348,178 B1
(45) Date of Patent: Mar. 25, 2008

(54) RECOMBINANT ADENOVIRAL VECTOR SYSTEM

(75) Inventor: Robert J. Schneider, New York, NY (US)

(73) Assignee: New York University Medical Center, New York, NY (US)

(*) Notice: Subject to any disclaimer, the term of this patent is extended or adjusted under 35 U.S.C. 154(b) by 874 days.

(21) Appl. No.: 08/733,611

(22) Filed: Oct. 17, 1996

Related U.S. Application Data

(63) Continuation of application No. 08/213,301, filed on Mar. 14, 1994, now abandoned.

(51) Int. Cl.
*C12N 15/63* (2006.01)
*C12N 15/64* (2006.01)
*C12N 15/861* (2006.01)
*C12N 15/87* (2006.01)
*A61K 48/00* (2006.01)

(52) U.S. Cl. .................... 435/456; 435/320.1; 435/455

(58) Field of Classification Search ............... 435/69.1, 435/172.1, 172.3, 173.3, 240.2, 320.1, 325, 435/366, 455, 456, 457; 536/23.1, 24.1, 536/23.72

See application file for complete search history.

(56) References Cited

U.S. PATENT DOCUMENTS 5,882,877 A * 3/1999 Gregory et al. ........... 435/320.1

OTHER PUBLICATIONS

Grable et al. "cis and trans Requirements for the Selective Packaging of Adenovirus Type 5 DNA", J. of Virol., Feb. 1992, vol. 66, No. 2, pp. 723-731.*
Stratford-Perricaulet et al. "Gene Transfer into Animals: The Promise of Adenoviruses", Human Gene Transfer, vol. 219, 1991, pp. 51-61.*
Mitani et al., "Rescue, propagation, and partial purification of a helper virus-dependent adenovirus vector", PNAS, vol. 92, pp. 3854-3858, Apr. 1995.*
Bhatti, A. and Weber, J., 1979, "Protease of Adenovirus Type 2: Partial Characterization", Virology 96:478-485.
Tibbetts, C. and Glam, C-Z., 1979, "In Vitro Association of Empty Adenovirus Capsids with Double-Stranded DNA", J. Virol. 32:995-1005.
Stillman, B. et al., 1981, "Identifiation of the Gene and mRNA for the Adenovirus Terminal Protein Precursor", Cell 23:497-508.
Saito, I. et al., 1985, "Construction of Nondefective Adenovirus Type 5 Bearing a 2.8-Kilobase Hepatitis B Virus DNA Near the Right End of its Genome", J. Virol. 54:711-719.
Haj-Ahmad, Y. and Graham, F., 1986, "Development of a Helper-Independent Human Adenovirus Vector and Its Use in the Transfer of the Herpes Simplex Virus Thymidine Kinase Gene", J. Virol. 57:267-274.

Kosturko, L. and Vanech, M., 1986/87, "In Vitro Encapsidation of Plasmid DNA into Human Adenovirus Empty Capsids", Virus Research 6:123-132.
Ghosh-Choudhury, G. et al., 1987, "Protein IX, a Minor Component of the Human Adenovirus Capsid, is Essential for the Packaging of Full Length Genomes", EMBO J. 6:1733-1739.
Hearing, P. et al., 1987, "Identification of a Repeated Sequence Element Required for Efficient Encapsidation of the Adenovirus Type 5 Chromosome", J. Virol. 61:2555-2558.
Prevec, L. et al., 1990, "A Recombinant Human Adenovirus Vaccine Against Rabies", J. Infect. Dis. 161:27-30.
Eloit, M. et al., 1990, "Construction of a Defective Adenovirus Vector Expressing the Pseudorabies Virus Glycoprotein gp50 and Its Use as a Live Vaccine", J. Gen. Virol. 71:2425-2431.
Vernon, S. et al., 1991, "Ultrastructural Characterization of Human Immunodeficiency Virus Type 1 Gag-Containing Particles Assembled in a Recombinant Adenovirus Vector System", J. Gen. Virol. 72:1243-1251.
Grable, M. and Hearing, P., 1992, "cis and trans Requirements for the Selective Packaging of Adenovirus Type 5 DNA", J. Virol. 66:723-731.
Lucito, R. and Schneider, R., 1992, "Hepatitis B Virus X Protein Activates Transcription Factor NF-xB Without a Requirement for Protein Kinase C", J. Virol. 66:983-991.
Berkner, K., 1992, "Expression of Heterologous Sequences in Adenoviral Vectors", Curr. Topics in Microbiol. Immunol. 158:39-66.
Rosenfeld, M. et al., 1991, "Adenovirus-Mediated Transfer of a Recombinant α1-Antitrypsin Gene to the Lung Epithelium in Vivo", Science 252:431-434.
Wilkinson, G. and Akrigg, A., 1992, "Constitutive and Enhanced Expression from the CMV Major IE Promoter in a Defective Adenovirus Vector", Nucl. Acids Res. 20:2233-2239.
Le Gal La Salle, G. et al., 1993, "An Adenovirus Vector for Gene Transfer into Neurons and Glia in the Brain", Science 259:988-990.
Zabner, J. et al., 1993, "Adenovirus-Mediated Gene Transfer Transiently Corrects the Chloride Transport Defect in Nasal Epithelia of Patients with Cystic Fibrosis", Cell 75:207-216.

* cited by examiner

*Primary Examiner*—David Guzo
(74) *Attorney, Agent, or Firm*—Jones Day

(57) ABSTRACT

The present invention relates to a novel Ad based packaging system that can be used for incorporation of heterologous DNA into infectious but replication defective viral particles. The components of the invention include an "artificial genome", i.e., a recombinant vector which contains elements that function as adenovirus replication and packaging signals flanking an intervening DNA sequence. The elements may comprise the minimum genomic Ad sequences required to direct replication of heterologous DNA and packaging into viral particles. The system also includes a means for expressing complementing helper functions to provide in trans viral proteins required for replication and packaging of recombinant viral vectors, but without contaminating the stock of recombinant, trans-packaged viral particles.

17 Claims, 7 Drawing Sheets

Figure 1:
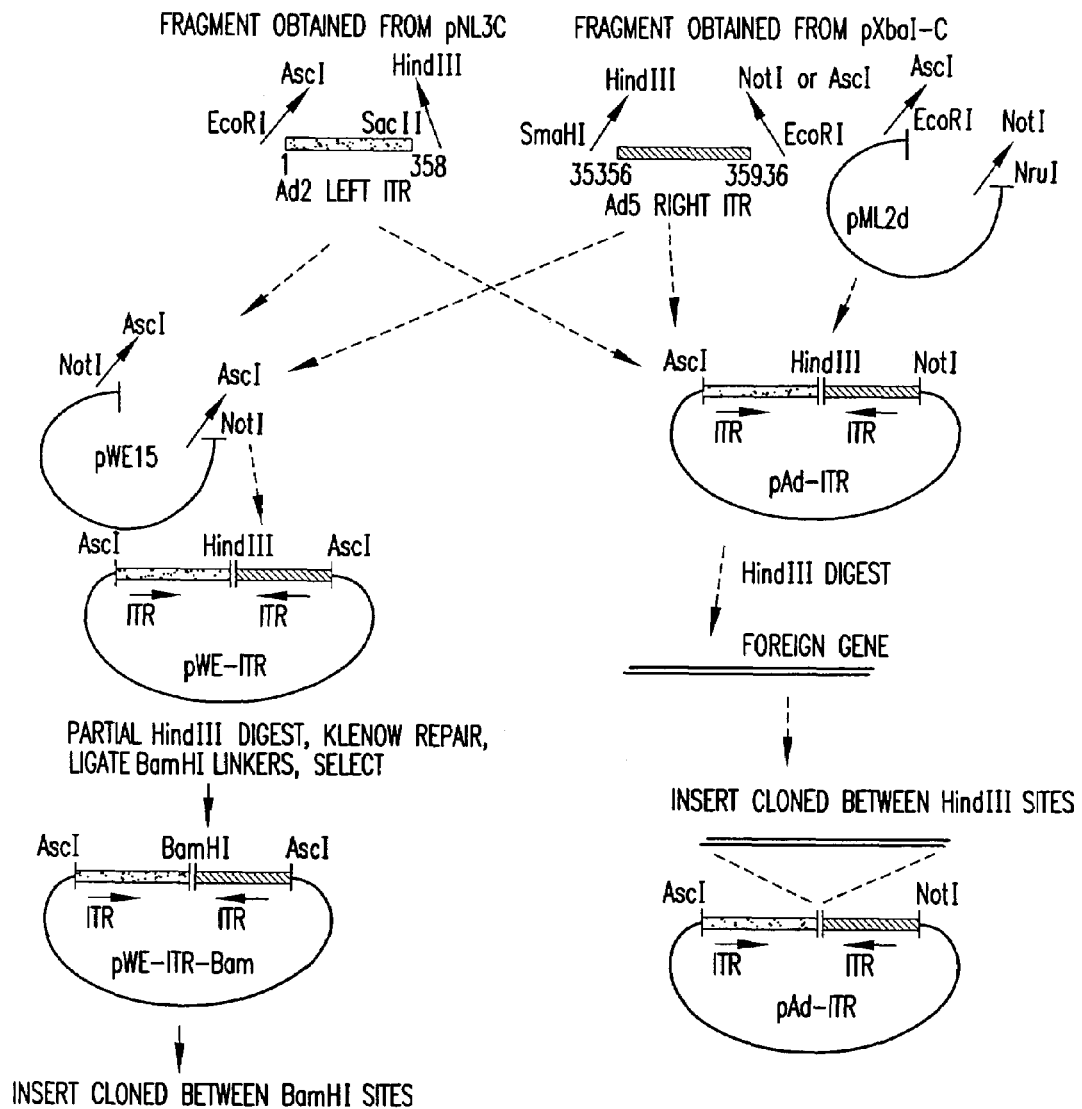

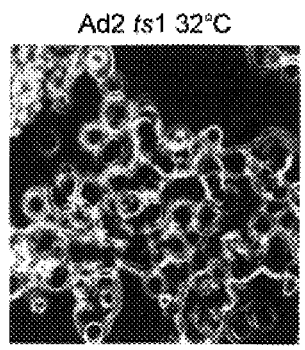
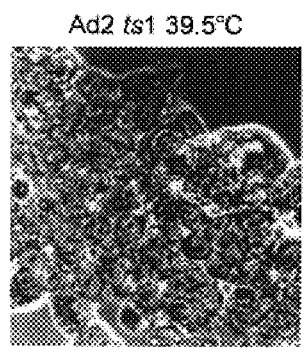
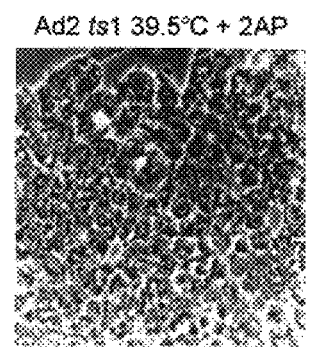
FIG.6A     FIG.6B     FIG.6C
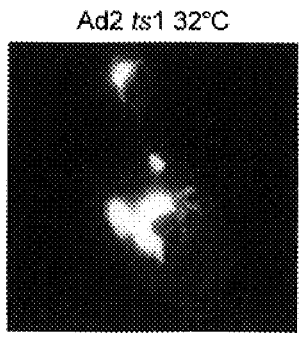
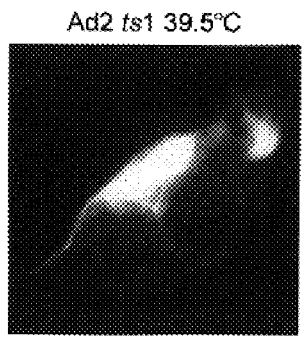
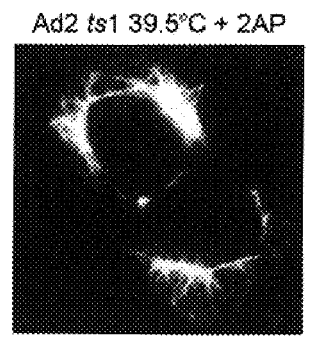
FIG.6D     FIG.6E     FIG.6F

RECOMBINANT ADENOVIRAL VECTOR SYSTEM

This application is a continuation of U.S. application Ser. No. 08/213,301, filed Mar. 14, 1994 now abandoned.

1. INTRODUCTION

The present invention relates to a novel adenovirus (Ad) based trans-packaging system for replication and encapsidation of recombinant DNA into viral particles. The system involves the use of recombinant viral vectors containing the minimum genomic adenovirus sequences required for replication and packaging of heterologous DNA into adenoviral particles. In addition, the invention relates to novel methods of providing helper viral functions which lead to selective and efficient packaging of DNAs in adenoviral particles. The novel recombinant viral vectors can be used, concurrently with the trans-packaging system, as a means of obtaining recombinant viral particles incapable of sustaining infectious replication that may be used to introduce DNA molecules in gene therapy.

2. BACKGROUND OF THE INVENTION

2.1. Gene Therapy

Recent progress in the areas of molecular biology and genetic engineering have led to the isolation and characterization of many genes associated with genetic diseases. This in turn has led to the development of the concept of gene therapy i.e., the replacement or supplementation of defective genetic information by transfer of normal functional genes, as a potential method for treating genetic disorders.

Currently available methods for transfer of genes into cells include chemical techniques such as direct calcium phosphate coprecipitation of DNAs into cells; mechanical techniques such as microinjection of cells with genetic materials; and membrane fusion-mediated transfer of genes via liposomes. The principle disadvantage associated with each of these techniques is that they are not practical for in vivo gene therapy applications, and the transfer of genetic material is often non-stable, and successful transfer is unpredictable. In an attempt to circumvent this problem, recent approaches for gene therapy have involved gene transfer using recombinant viral vectors, exploiting RNA and DNA tumor viruses. Many of these viruses are pathogenic and capable of causing disease. It has been proposed that these viruses could be genetically manipulated to deprive them of deleterious characteristics while maintaining their usefulness for possible introduction of stable, inheritable and functional genetic information by infection of cells.

The retroviruses represent one class of viruses that have been extensively studied for use in gene therapy (Miller, A.D., 1990, Human Gene Ther. 1:5-14). Unfortunately, there are a number of disadvantages associated with retroviral use, including the random integration of retroviruses into the host genome which may lead to insertional mutagenesis, or the inadvertent activation of protooncogene expression due to the promoter activity associated with retroviral LTRs (long terminal repeats). The Adeno-associated viruses have also been studied as an alternative system for delivery of stable genetic information into the cell. These viruses have the desirable feature of potentially integrating in specific regions of the host genome. However, the usefulness of both retroviral and AAV vectors is limited by their inability to accept heterologous DNA fragments greater than 3-5 Kb, the inability to produce larger quantities of viral stocks, and in the case of retroviruses, instability.

2.2. Adenovirus Based Vectors

Adenovirus (Ad) is a large, nonenveloped virus consisting of a dense protein capsid and a large linear (36 kb) double strand DNA genome. Adenovirus infects a variety of both dividing and non-dividing cells, gaining entry by receptor-mediated uptake into endosomes followed by internalization. After uncoating, the Ad genome expresses a large number of different gene products that are involved in viral replication, modification of host cell metabolism and packaging of progeny viral particles. Three Ad gene products are essential for replication of viral genomes: the terminal binding protein which primes DNA replication, the viral DNA polymerase, and the DNA binding protein (reviewed in Tamanoi and Stillman, 1983, Immunol. 109:75-87). In addition, processing of the terminal binding protein by the Ad 23kDa L3 protease is required to permit subsequent rounds of reinfection (Stillman et al., 1981, Cell, 23:497-508) as well as to process Ad structural proteins, permitting completion of self-assembly of capsids (Bhatti and Weber, 1979, Virology, 96:478-485).

Packaging of nascent Ad particles takes place in the nucleus, requiring both cis-acting DNA elements and trans-acting viral factors, the latter generally construed to be a number of viral structural polypeptides. Packaging of adenoviral DNA sequences into Ad capsids requires the viral genomes to possess functional Ad encapsidation signals, which are located in the left and right termini of the linear viral genome (Hearing et al., 1987, J. Virol. 61:2555-2558). Additionally, the packaging sequence must reside near the ends of the viral genome to function (Hearing et al., 1987, J. Virol. 61:2555-2558; Grable and Hearing, 1992, J. Virol., 66:723-731). The E1A enhancer, the viral replication origin, and the encapsidation signal compose the duplicated inverted terminal repeat (ITR) sequences located at the two ends of Ad genomic DNA. The replication origin is loosely defined by a series of conserved nucleotide sequences in the ITR which must be positioned close to the end of the genome to act as a replication-priming element (reviewed in Challberg and Kelly, 1989, Biochem, 58:671-717; Tamanoi and Stillman, 1983, Immunol. 109:75-87). As shown by several groups, the ITRs are sufficient to confer replication to a heterologous DNA in the presence of complementing Ad functions. Ad "mini-chromosomes" consisting of the terminal ITRs flanking short linear DNA fragments (in some cases non-viral DNAs) were found to replicated in vivo at low levels in the presence of infecting wild-type Ad, or in vitro at low levels in extracts prepared from infected cells (e.g., Hay et al., 1984, J. Mol. Biol. 175:493-510; Tamanoi and Stillman, 1983, Immunol. 109:75-87). Evidence for trans-packaging of mini-chromosomes was not reported in these or any later studies concerned with mechanisms of Ad DNA replication, and it is unlikely that packaging occured for several reasons. First, the replicated molecules were quite small, and they were not expressed at levels high enough to compete for packaging. Second, no selection for trans-packaging was employed, making it inconceivable that the heterologously replicated molecules could compete for packaging against wild-type Ad genomes.

The expression of foreign genes in "replication-defective" Ad viruses (deleted of region E1) has been exploited for a number of years in many labs, and a variety of published reports describe several different approaches often used in constructing these vectors (Vernon et al., 1991, J. Gen. Virol., 72:1243-1251; Wilkinson and Akrigg, 1992, Nuc.

Acids Res., 20:2233-2239; Eloit et al., 1990, J. Gen. Virol., 71:2425-2431; Johnson, 1991; Prevec et al., 1990, J. Infect. Dis., 161:27-30; Haj-Ahmad and Graham, 1986, J. Virol., 57:267-274; Lucito and Schneider, 1992, J. Virol., 66:983-991; reviewed in Graham and Prevec, 1992, Butterworth-Heinemann, 363-393). In general, replication-defective viruses are produced by replacing part or all of essential region E1 with a heterologous gene of interest, either by direct ligation to viral genomes in vitro, or by homologous recombination within cells in vivo (procedures reviewed in Berkner, 1992, Curr. Topics Micro. Immunol., 158:39-66). These procedures all produce Ad vectors that replicate in complementing cell lines such as 293 cells which provide the E1 gene products in trans. Replication competent Ad vectors have also been described that have the heterologous gene of interest inserted in place of non-essential region E3 (e.g., Haj-Ahmad and Graham, 1986, J. Virol. 57:267-274), or between the right ITR and region E4 (Saito et al., 1985, J. Virol., 54:711-719). In both replication defective viruses and replication competent viruses, the heterologous gene of interest is incorporated into viral particles by packaging of the recombinant Ad genome. To demonstrate the feasibility of correcting defects in α-1 AT deficiency or cystic fibrosis, replication-defective Ad vectors expressing the α-1 antitrypsin gene and the CFTR gene, respectively, were used to deliver foreign genes to the lungs of cotton rats by injection of viruses (Rosenfeld et al., 1991, Science, 252:431-434; Rosenfeld et al., 1992, Cell, 252:431-434; Zabner et al., 1993, Cell 75:207-216). In addition, a replication-defective Ad vector expressing β-galactosidase, in place of the region E1, was directly injected into mouse brain and found to nonproductively infect glial and neuronal cells (LaSalle et al., 1993, Science, 259:988-990).

A number of potential drawbacks can be attributed to the use of currently available adenovirus systems, such as the strict controls on the size of the genome that can be packaged. Adenovirus genomes cannot exceed 103-104% the normal 36 kb length (i.e. ~2 kb extra; Ghosh-Choudhury et al., 1987, EMBO J. 6:1733-1739). Therefore, recombinant viruses deleted of region E1 and/or E3 can only accommodate foreign DNA inserts of up to 6-7 kb (reviewed in Berkner 1992, supra). This precludes the use of Ad vectors for introduction of large DNA fragments such as genomic DNAs and complex regulatory units generally required for sophisticated tissue expression.

In addition, conventional replication-defective Ad recombinants which have the E1 region deleted, have been used with the belief that deletion of region E1 (either partially or entirely) will prevent expression of other Ad genes. Although region E1 is required to activate expression of the Ad genome, there is a body of evidence indicating that at high multiplicities of infection or in certain cell types, viral replication and cytopathic effects (CPE) are occasionally observed even in the absence of E1A gene expression (e.g., Eloit et al., 1990, J. Gen. Virol, 71:2425-2431; Postlethwaite, 1973, Scott. Med. J., 18:131).

Another potential drawback is that early Ad genes other than E1A have been shown to cause pathology in the lungs of cotton rats, which have served as an animal model for human infection. Infection with a virus that expresses Ad early regions but does not replicate causes significant cytopathology, although not as severe as wild-type replicating viruses (Ginsberg et al., 1990, Proc. Natl. Acad. Sci. USA, 87:6191-6195). Finally, with the currently available Ad systems the potential exists for creation of an "escape" wild-type virus resulting from recombination between the recombinant Ad vector and natural infection by helper viral DNA sequences. Recombination during natural infection between the vector and endogenous Ads can result in restoration of autonomous replication to the vector and creation of unanticipated viral variants, a real and alarming possibility inherent in current gene therapy applications.

Trans-packaging systems specific for Ad-recombinants might solve a number of the drawbacks associated with the use of adenoviral systems. However, trans-packaging systems specific for Ad-based genomes have not been described before. Although bacteriophage packaging systems have been in wide use for years (e.g., Feiss and Becker, 1983, Lambda II, Cold Spring Harbor Press, 305-330), unlike bacterial viruses, the ability to trans-package Ad DNA genomes appears to be more complicated and precisely controlled, and approaches used successfully for bacteriophage systems have not worked for Ad (Kosturko and Vanech, 1986, Virus Res., 6:123-132).

Several studies have been published attempting to produce in vitro (cell-free) extracts for trans-packaging of heterologous DNAs into empty Ad virus capsids, akin to those described for bacteriophage systems (Tibbetts and Giam, 1979, J. Virol. 32:95-105; Kosturko and Vanech, 1986, Virus Res., 6:123-132). However, specific encapsidation of heterologous DNAs into Ad capsids has not been achieved.

3. SUMMARY OF THE INVENTION

The present invention relates to a novel Ad based packaging system that can be used for incorporation of heterologous DNA into infectious but replication defective viral particles. The components of the invention include an "artificial genome", i.e., a recombinant vector which contains elements that function as adenovirus replication and packaging signals flanking an intervening DNA sequence. The elements may comprise the minimum genomic Ad sequences required to direct replication of heterologous DNA and packaging into viral particles. The system also includes a means for expressing complementing helper functions to provide in trans viral proteins required for replication and packaging of recombinant viral vectors, but without contaminating the stock of recombinant, trans-packaged viral particles.

The invention is based, in part, on the discovery that all Ad functions required for replication of artificial genomes, production of viral particles, and encapsidation of genomes can be supplied in trans to recover and purify encapsidated artificial genomes, provided that the following parameters are controlled: (1) the artificial genome is engineered to an appropriate size; (2) the helper DNA is engineered to minimize or eliminate contamination from the complementing source, including but not limited to using helper DNA that is too large to be packaged, helper DNA which contains mutated encapsidation on sequences, or helper DNA which lacks encapsidation sequences; and (3) genetic and biochemical approaches are engineered to minimize the loss of cell viability during expression of Ad gene products required for replication and encapsidation of the artificial genomes; including but not limited to engineering mutations in the L3-23kDa protease, or by biochemical inhibition of Ad induced CPE using any of several agents described herein.

The invention is illustrated by working examples describing the construction and use of artificial genomes and vectors which supply helper functions in trans.

4. DESCRIPTION OF THE FIGURES

FIG. 1. Construction of artificial genomes for trans-packaging containing the left and right Ad inverted terminal repeat (ITR) structures.

Figure 2:
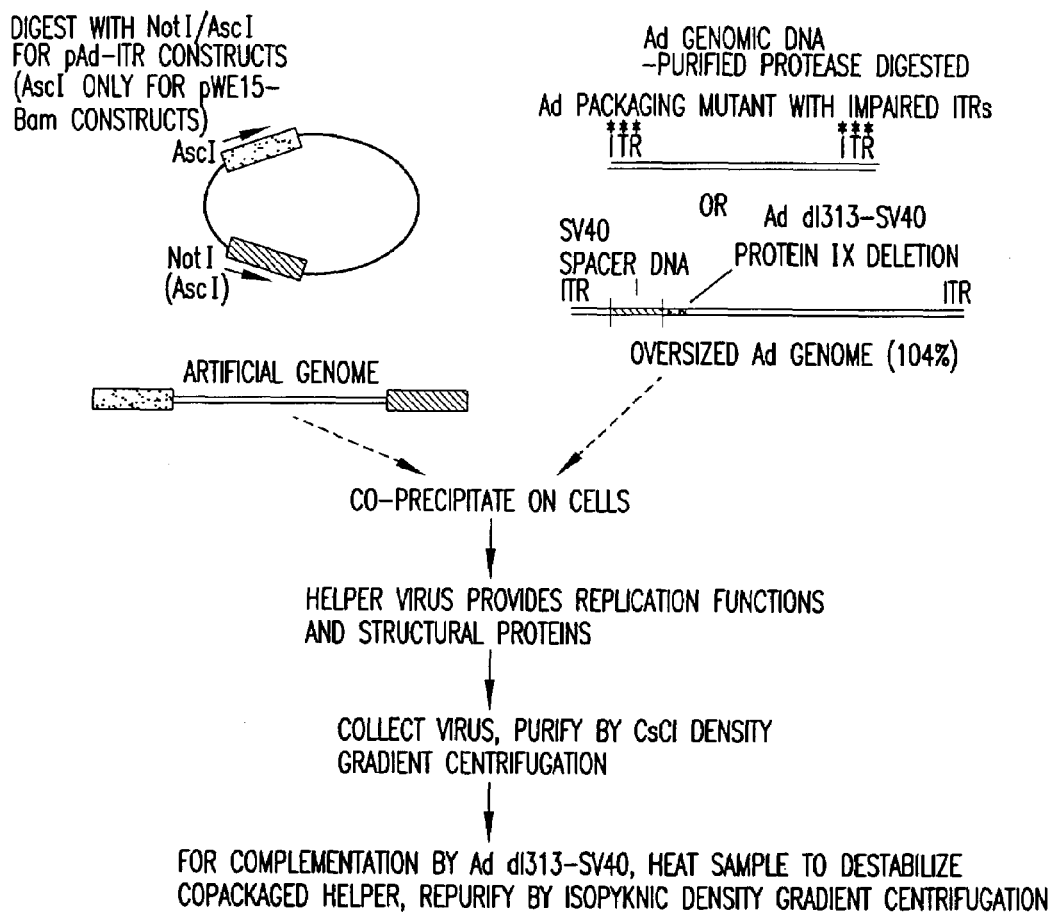

FIG. 2. Helper virus mediated complementation and trans-packaging of artificial genomes.

Figure 3:
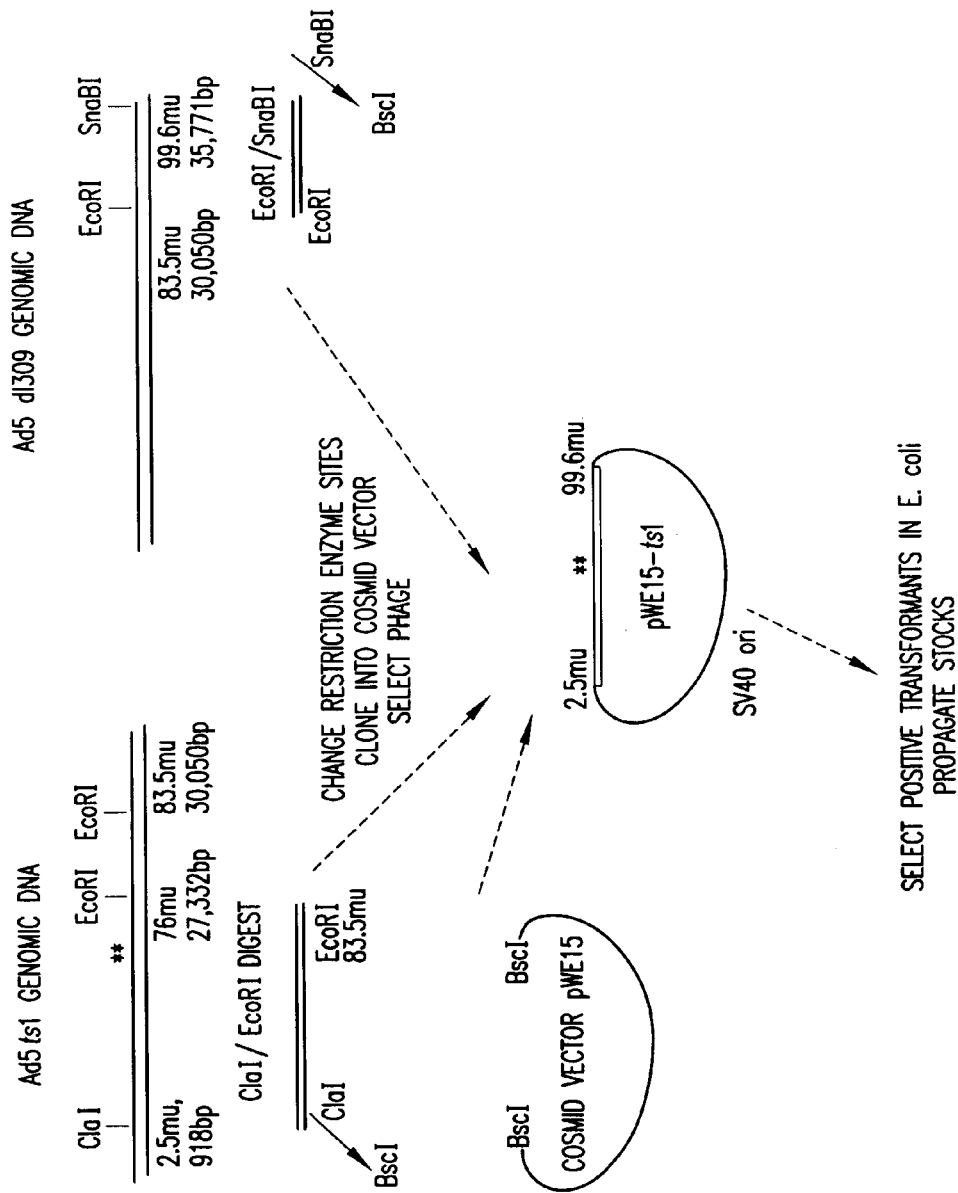

FIG. 3. Construction of cosmid to complement adenovirus gene functions.

Figure 4:
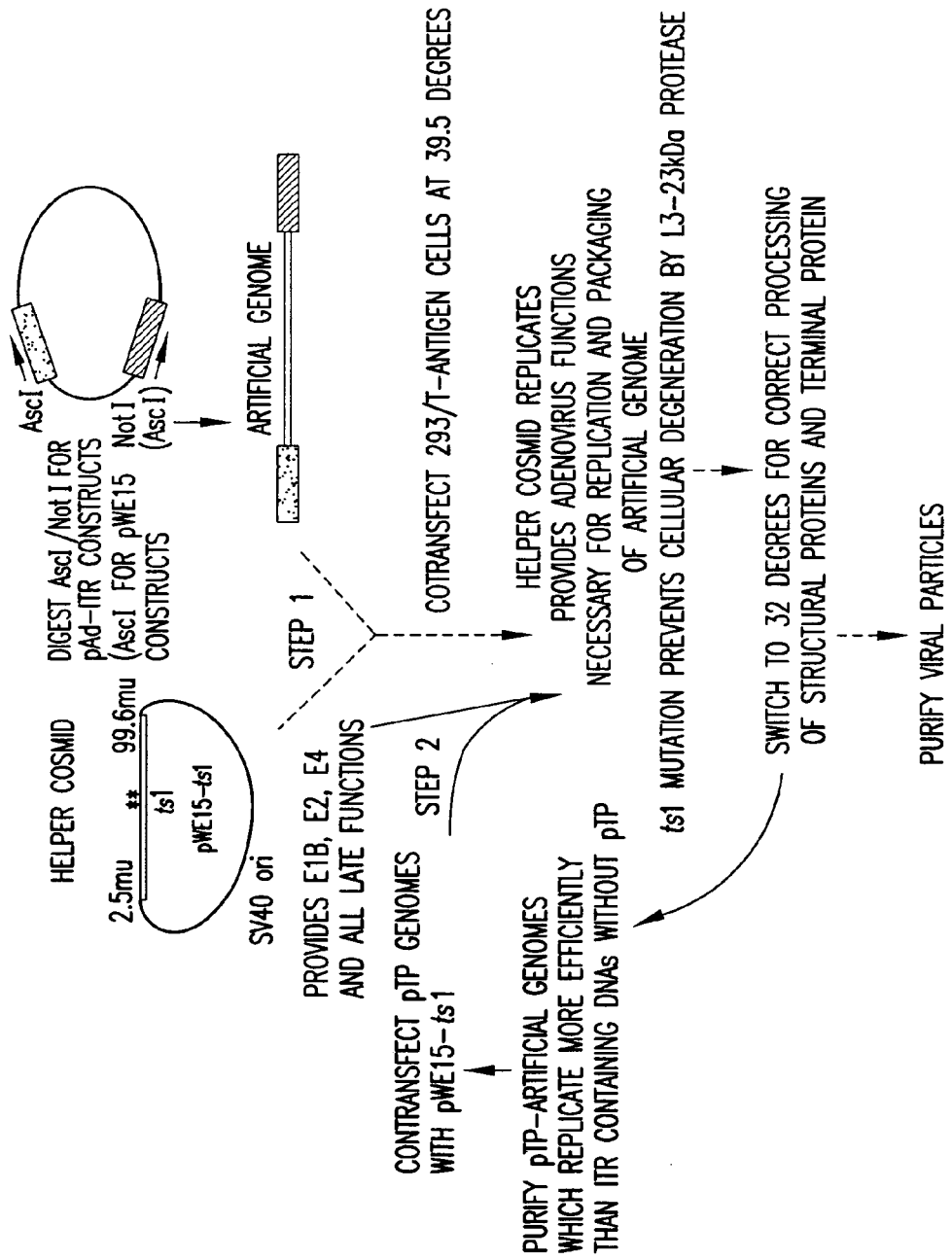

FIG. 4. Helper-free mediated trans-packaging of adenovirus particles containing artificial genomes.

Figure 5:
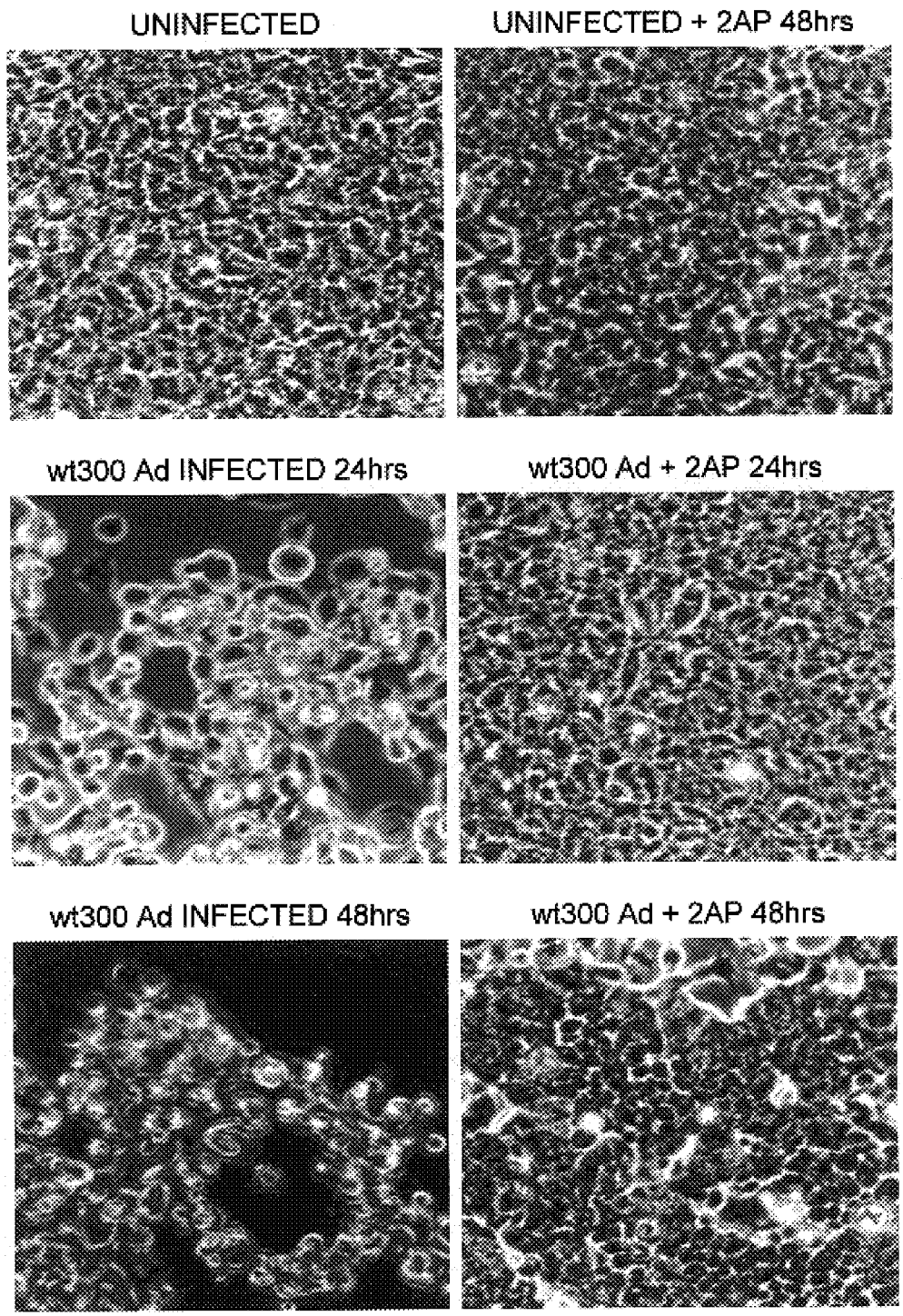

FIG. 5. Prevention of adenovirus induced CPE and facilitated cell lysis or loss of metabolic function during expression of late viral genes. Cells were infected at 50 PFU per cell with wild type Ad, and 20 mM 2-aminopurine (2AP) was added to duplicate plates 2 h post infection for up to 48 h. Cells were photographed at 24 and 48 h. 2AP treatment of uninfected 293 cells had little detectable cytotoxicity at 48 h posttreatment as shown and largely prevented detectable CPE in wild type Ad-infected cells observed as late as 48 h post infection. Late Ad polypeptides can therefore be expressed in this system for the duration of several days without facilitating cell lysis and CPE that would limit their expression.

FIG. 6. Ad induced cell CPE linked to disruption of the cytokeratin network and coupled shutoff of host translation can be largely prevented. 293 cells were infected with Ad2 ts1 at 4,000 particles per cell, a 25 plaque forming unit (PFU) per cell equivalent, given the high particle/PFU ratio for this mutant, in the presence or absence of 2AP at 32° C. or 39.5° C. Cells infected with wild type Ad at 39.5° C. displayed identical viral growth kinetics as those infected at 37° C. Cells were fixed and processed for indirect immunofluorescence, using a keratin K18-specific antibody. Cells infected at 32° C. were fixed at 40 h post infection, cells infected at 39.5° C. were fixed at 22 h post infection. By preventing Ad viral proteolysis of keratin K18, viral induced CPE and early cell lysis can be controlled.

Figure 7:
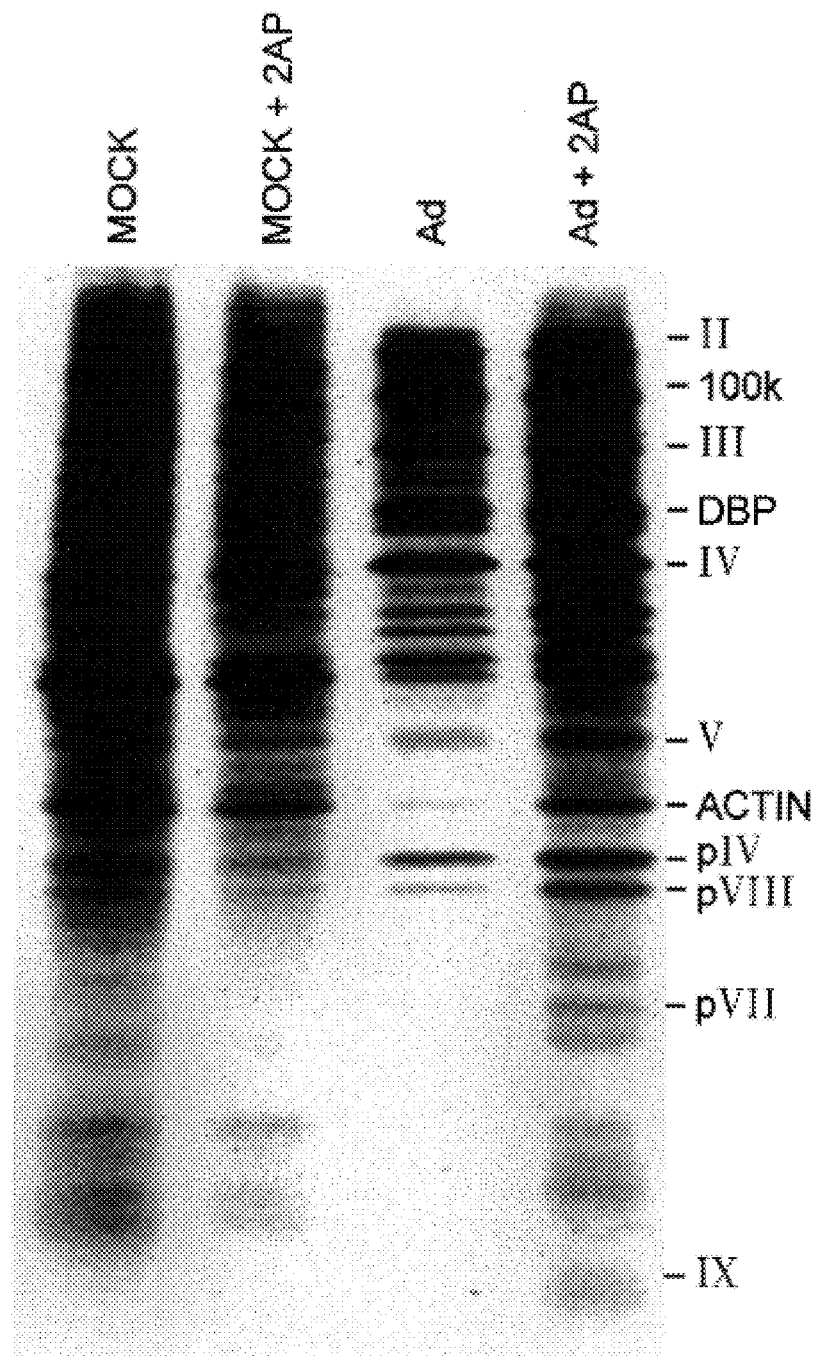

FIG. 7. 2AP prevents the shutoff of translation of cellular and early Ad mRNAs. Uninfected and wild type Ad-infected 293 cells were labeled with [$^{35}$S]methionine at 24 h post infection and duplicate plates were treated with 10 mM 2AP, added 1 to 2 h after infection. Equal amounts of protein from labeled extracts were analyzed by SDS-polyacrylamide gel electrophoresis and fluorographed. Ad late polypeptides correspond to proteins II, III, IV, V, pIV, pVIII, pVI, and IX.

5. DETAILED DESCRIPTION OF THE INVENTION

The present invention relates to a method for producing stocks of recombinant adenovirus and is directed towards producing a viral vector system that is efficient and safe relative to other viral vector systems currently used. The method of the invention utilizes a two component system comprising (i) a recombinant adenovirus vector which contains heterologous DNA sequences of interest and cis-acting sequences (e.g., viral ITR sequences or functionally, equivalent sequences) required for replication and packaging of said vectors (hereinafter referred to as the "artificial genome"); and (ii) trans-acting viral functions necessary for replication and encapsidation of the recombinant vector.

The artificial genomes of the invention contain the minimum cis-acting sequences necessary for replication and packaging of the recombinant DNA thereby permitting the insertion of large fragments of DNA of interest (~15 to >30 Kb) while retaining the ability to be efficiently packaged. In addition, the trans-packaged recombinant Ad vectors need not contain Ad coding sequences, thereby circumventing possible pathological effects related to expression of adenovirus genes in the host cells which is an authentic risk inherent in current Ad vector systems.

The various methods described herein for providing helper function have been designed to maximize the expression and usefulness of trans-acting viral proteins needed for replication and encapsidation of the recombinant vector DNA while simultaneously reducing their deleterious effects to the host cells that participate in trans-packaging of artificial genomes. These methods, coupled with the impaired packaging of the helper DNA due to mutation or deletion of terminal repeat sequences, results in an effective packaging system for generation of recombinant viral particle stocks.

5.1. Construction of Artificial Genomes

The artificial genomes of the present invention include any recombinant DNA molecule which incorporates sufficient regions of the Ad-inverted terminal repeat structures (ITRS), or other elements that are functionally equivalent, to permit replication and packaging of the recombinant molecule into virus particles. The artificial genome itself need not contain Ad genes encoding Ad proteins, including those associated with DNA or RNA synthesis or any step of viral replication including capsid formation. In preferred embodiments of the invention, the artificial genomes retain only the Ad terminal repeat sequences necessary for replication and packaging of recombinant DNA.

Functional terminal repeat structures of any Ad serotype may be used in the practice of the invention. In a specific embodiment of the invention described in the working examples herein, recombinant vectors were generated which contain DNA fragments corresponding to the Ad2 left terminal repeat sequence (nucleotides 1-358) and Ad5 right terminal repeat sequence (nucleotides 35356-35936). However, functional terminal repeat structures found in Ad serotypes other than Ad2 or Ad5 may be used equally well in the practice of the invention.

Derivatives of the Ad terminal repeats or other elements can also be used in the present invention, as long as they retain the ability to provide information in cis for the replication and packaging of recombinant DNA into viral particles. In particular, terminal repeat derivatives can be made by altering the terminal repeat sequences by substitutions, additions, or deletions which provide for functionally active molecules. Elements that could perform a function equivalent to the ITRs include repeated A/T-rich elements placed no more than ~400bps from the termini that may mimic Ad packaging elements, and GC-rich motifs located close to the termini which may mimic Ad replication signals.

According to the invention, the recombinant Ad terminal repeat structures are inserted into recombinant vectors which contain sequences necessary for replication in appropriate host cells in order to obtain large quantities of recombinant vector DNA, i.e., as part of plasmids, cosmid or bacteriophage, or other viruses used in appropriate host cells, etc. Standard recombinant DNA methods may be used for insertion of Ad terminal repeat structures into vectors (Sambrook et al., 1989, Cold Spring Harbor, N.Y. Cold Spring Harbor Laboratory Press).

For example, the terminal repeat structures may be amplified in a PCR reaction using oligonucleotide primers that add appropriate restriction endonuclease recognition sites onto each end of the amplified DNA fragment. Alternatively, any restriction site desired may be produced by ligating nucleotide sequences (linkers), comprising specific chemically synthesized oligonucleotides encoding restriction endonuclease recognition sequences, onto the termini of the amplified Ad ITR fragments.

In practicing the present invention, it is important to be able to linearize the artificial genome and liberate the Ad terminal repeats for subsequent replication and encapsidation of the recombinant DNA into viral particles. Liberation of the termini is required for recognition of the Ad origin of replication (van Bergen et al., 1983, Nuc. Acids Res. 11:1975-1989) and for proper spatial placement of the encapsidation signal (Grable & Hearing, 1992, J. Virol., 66:723-731). Accordingly, the artificial genomes of the present invention should contain unique restriction endonuclease sites immediately flanking, externally, both terminal repeat structures. In addition, the two terminal repeat structures should be joined internally with one or more unique cloning sites which may be used to insert the heterologous DNA of interest.

The artificial genomes of the present invention may incorporate any heterologous DNA from a variety of sources, including genes or portions of genes. In the present invention, the DNA insert may be quite large provided it can be packaged by Ad. It is known that there are strict controls on the size of Ad genomes that can be packaged, and that viral genomes that exceed 103-104% of the wild type adenovirus 36 kb genome length are packaged very poorly. These guidelines may be applied to the size of the artificial genome used in accordance with the invention. Thus, artificial genomes up to approximately 39 kb in size may be inserted into the recombinant vectors using standard cloning methodologies (Sambrook et al., 1989, Cold Spring Harbor, NY:Cold Spring Harbor Laboratory Press). Depending upon the helper virus used, artificial genomes ranging from 10 kb to 36 kb may be preferred, with 25 kb to 36 kb more preferred.

If the foreign DNA of the artificial genome is to be transferred to and expressed in host cells, the appropriate transcriptional/translational control sequences and polyadenylation signals may be provided to control expression of the gene of interest. A variety of promoter/enhancer elements may be used depending on the level and tissue specific expression desired. The promoter/enhancer may be constitutively expressed, inducible or may, alternatively be tissue specific.

In a specific embodiment of the invention described in the working examples, a vector was constructed as diagrammed in FIG. 1, which contained the left and right terminal repeat (ITR) sequences, in this case from Ad2 and 5, inserted into a plasmid (pML2d) or a cosmid (pWEI5). A unique HindIII or BamH1 restriction enzyme site joins the two ITRs, which are flanked by AscI/NotI sites in one construct and AscI sites in another. These constructs permit insertion of heterologous DNAs between the ITR elements using the unique cloning site (HindIII or BamH1), as well as the ability to precisely linearize the plasmid close to the termini of both ITRs.

5.2. Recombinant Helper DNA

One aspect of the present invention relates to a method of producing stocks of the packaged artificial genome. The resulting stocks are infectious, thus allowing for introduction of the DNA of interest, but are not capable of autonomous replication. The method utilizes a two component system comprised of (1) the artificial genome; and (2) a helper DNA which provides those trans-acting viral functions necessary for replication and encapsidation not encoded by the artificial genome.

The helper DNA of the invention comprises Ad DNA which is capable of providing in trans the functions necessary for replication and packaging of the artificial genomes into infectious viral particles. The helper DNA may be provided as Ad genomic DNA, as Ad DNA cloned into recombinant vectors to allow for propagation in appropriate host cells such as microorganisms, or as Ad DNA stably transfected into host cells that stably express the helper functions.

Ideally, the helper DNA itself is not incorporated into viral particles. Helper DNA may be excluded from viral particle formation by virtue of its failure to be packaged into infectious viral particles. Various methods are described below for providing helper function while minimizing or preventing the incorporation of helper DNA into infectious viral particles.

5.2.1. Ad Genomic DNA Helper Systems

In one embodiment of the invention, helper DNA comprised of Ad genomic DNA containing mutations in the cis-acting packaging signals may be used to provide the necessary trans-acting factors (FIG. 2). Because of the mutations in the packaging signals these particular helper DNAs will not be efficiently assembled into virions. Various packaging mutants have been described which are up to 140 fold deficient in packaging as compared to wild type. In a specific embodiment of the invention described in the working examples, infra, packaging mutants which are severely deficient in packaging are used. (Grable & Hearing, 1992, J. Virol. 66:723-731).

In another embodiment of the invention, size can be used to control or limit packaging of the helper DNA; i.e., helper DNA that is too large to be packaged efficiently may be utilized. In this aspect of the invention, some packaging is required in order to propagate the helper DNA, however, when used in conjunction with the artificial genomes, the poor packaging efficiency of the oversized helper DNA results in enhanced packaging of the artificial genome. For example, helper DNA which is 103-104% the normal Ad genome size may be used to decrease the efficiency with which helper DNA is packaged. To this end any foreign DNA fragments may be used to increase the size of the helper DNA. As depicted in FIG. 2, a helper virus was constructed which contained the SV40 viral genome in place of the adenovirus E1 region and the protein IX gene which is required for viral particle stability when full-length and larger than genome-size DNAs are packaged. This virus replicates in complementing cell lines such as 293 cells that express E1a/E1b functions in trans, and it expresses adenovirus early and late genes, but due to its large size packaging of its own genome occurs at only roughly 2-5% the wild type level, and is more severely impaired by heating virus particles.

Packaging systems which utilize preparations of Ad genomic DNA for helper function may be further optimized by subjecting the purified genomic helper DNA to protease digestion and phenol chloroform extraction prior to use in the present packaging system. The deproteinization of the Ad genomic DNA results in removal of the covalently linked Ad terminal binding protein (pTP), which is required for DNA replication. This added step further ensures that the helper vector is not preferentially replicated and packaged over the artificial genomic DNA.

5.2.2. Helper Vectors and Cell Lines

While the foregoing genomic Ad DNA systems provide the required helper functions in trans for replicating and packaging the artificial genomes, they are not very efficient because propagation of the helper DNA is difficult. Thus, in yet another embodiment of the invention, helper functions are provided in trans by autonomously replicating plasmids that lack functional adenoviral replication and packaging elements. Such DNA may be propagated in microorganisms, for example, such as bacteria, yeast, insect cells or animal cells as part of a plasmid, cosmid, YAC bacteriophage or appropriate viral-based vectors. To this end, the entire adenovirus genome lacking functional replication and packaging elements, portions of the complementing adenovirus genome, or Ad cDNA coding for the required trans-acting factors may be incorporated into recombinant helper plasmids, bacteriophages, cosmids, YACs, etc. by methods well known in the art.

Various additions and modifications may be made to these particular vectors to increase the levels of expression of the adenovirus trans-acting factors. For example, DNA sequences that permit autonomous replication in mammalian cells may be inserted into the recombinant helper plasmids. Autonomous replication of these plasmids will increase the number of templates available for transcription of the helper DNA resulting in an increased production of viral replication and packaging proteins. Autonomous replication sequences that may be utilized include, but are not limited to those sequences found in viruses such as SV40, papilloma, or EBV. For example, helper activity may be provided by cloning the entire Ad genome (but without the ITR elements to avoid recombination with the artificial genome) into a plasmid capable of autonomous replication in the presence of SV40 T-antigen (FIG. 4). Autonomous replication is provided by insertion of the gene encoding the SV40 T-antigen into 293 cells which may be used in the packaging process (see Section 5.3, infra) (e.g. 293/T-Ag cells). Alternative eukaryotic expression systems which may be used to express the helper functions are yeast transformed with recombinant yeast expression vectors; insect cell systems infected with recombinant virus expression vectors (e.g., baculovirus); or plant cell systems infected with recombinant virus expression vectors (e.g., cauliflower mosaic virus, CaMV; tobacco mosaic virus, TMV) or transformed with recombinant plasmid expression vectors (e.g., Ti plasmid).

In another embodiment, cell lines may be engineered to stably express the helper functions. Stable expression can be accomplished using selectable and/or amplifiable markers to ensure integration of the DNA into the host cell chromosome. For example, following the introduction of DNA encoding the helper functions, engineered cells may be allowed to grow for 1-2 days in an enriched media, and then are switched to a selective media. Rather than using expression vectors which contain viral origins of replication, host cells can be transformed with DNA controlled by appropriate expression control elements (eg., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$ or $aprt^-$ cells respectively. Also, antimetabolite resistance can be used as the basis of selection for dhfr, which confers resistance to methotrexate (Wigler, et al., 1980, Natl. Acad. Sci. US 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072; neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

5.2.3. Improving Efficiency of the System

In yet another modification of this general approach the efficiency of trans-packaging of artificial genomes may be further improved. Only three Ad virus proteins are required for replication mediated by the Ad ITR elements (reviewed in Tamanoi and Stillman, 1983, Immunol. V1:109, 75-87); the 80 kd pTP and 140 kd polymerase encoded by region E2B, and the 72 kd DNA binding protein encoded by region E2A. For examples plasmids may be constructed encoding these two regions under the control of the SV40 origin of replication and early promoter. These plasmids may be cotransfected with the recombinant Ad vector DNA into 293/T-Ag cells. Several days later, after substantial replication of the recombinant Ad vector DNA has occurred, cells are infected with Ad packaging mutant d1309-L55, or transfected with the Ad genomic plasmid to provide structural polypeptides for formation of viral capsids. The amplification of Ad vector DNA prior to replication of the helper virus enhances the extent of Ad vector genomes trans-packaged into viral capsids.

A rate limiting effect likely associated with the use of adenovirus packaging systems is the inefficient expression and assembly of viral capsid proteins due to virally induced cytopathic effects which facilitates cell lysis, i.e., while efficient synthesis of viral structural proteins is occuring. For example, at the time of cell lysis or loss of metabolic integrity, the number of DNA molecules capable of being encapsidated into virus particles, and the amount of capsid proteins present, far exceeds the number of newly synthesized virus particles. It is therefore desirable to utilize a method that prevents or delays viral cytopathic effects, thereby increasing the time during which viral capsid proteins may be produced and assembled. This is particularly true for systems in which DNAs are introduced into cells by transfection, often necessitating that a long duration of synthesis be tolerated.

During a normal wild type Ad infection, the virally encoded L3-23k protease is responsible for proteolytic degradation of host cell cytokeratins K18 and K7. As shown in the working examples, infra, the degradation of these cellular cytokeratins leads to disruption of cellular intermediate filament networks and accelerates cell lysis or loss of metabolic function (see Section 6 infra). The L3-23k protease is also involved in proteolytic maturation of the pTP viral protein, and the maturation of several viral capsid proteins thereby permitting completion of viral particle assembly.

In an embodiment of the invention, an Ad helper DNA which contains a mutation in the viral gene encoding the viral L3-23 kDa protease may be used to suppress viral facilitated cell lysis or loss of viability thereby increasing the duration of expression of Ad gene products required for replication and packaging of recombinant Ad vectors. In a preferred embodiment of the invention, Ad2ts1 mutant genomic DNA, which is temperature sensitive for the L3 protease may be used to provide helper function. Alternatively, the Ad2ts1 mutant helper DNA may be cloned into a vector that is propagated in microorganisms, for example, as part of a bacterial plasmid, cosmid or bacteriophage. In the working examples described infra, the Ad2ts1 mutant genome which is temperature sensitive for L3-23 kDa protease activity at restrictive temperatures (39.5° C.) but not at permissive temperatures (32° C.) (Bhatti and Weber, 1979, Virology, 96:478-485) is cloned into a vector containing the SV40 origin of replication as depicted in FIG. 3. Transfection of this plasmid into 293/T-Ag cells at 39.5° C. results in high levels of plasmid replication and expression of Ad genes encoding replication and capsid proteins. However, since L3 protease is inactive, maturation and final assembly of virus particles is postponed until cells are placed at permissive temperatures. Since the plasmid contains a helper virus genome without sequences overlapping that of the recombinant Ad genome, recombination cannot take place between the two DNA fragments to restore wild-type virus. Thus, this plasmid provides a high level of expression of Ad gene products required for replication and packaging of artificial genomes but cannot itself be packaged, and provides these helper functions without facilitating lysis of cells or loss of cell viability which reduces virus yields (FIG. 4). This approach maintains cellular integrity at restrictive temperatures, resulting in higher yields of trans-packaged virus particles and in addition obviates the need to purify helper virus particles from those containing artificial genomes.

In packaging systems which use helper DNA containing non-temperature sensitive or deletion mutations in the L3 protease, the L3 protease function may be provided in several ways. 293/T-Ag cell lines expressing L3-23kDa functions can be constructed in which expression of the protease is maintained under tight regulation. Alternatively, L3-23k protease can be provided in trans by transfection of an expression vector, which places the L3 gene under the control of an mammalian cell inducible promoter, into the packaging cell cultures. A variety of inducible promoters and regulatory systems may be used in the practice of the invention, which include but are not limited to the heat shock, metallothionine or tetracycline regulated promoters. Regulated promoters may be linked to translational regulatory elements, such as the iron-responsive element.

Adenovirus infection results in a variety of metabolic defects including the inhibition of host cell protein synthesis. One consequence associated with viral mediated inhibition of host protein synthesis is that the cell is unable to synthesize cytokeratins to replace those cleaved by the viral L3 protease, as well as other proteins required to maintain basic metabolic functions important for viability. In yet another embodiment of the invention, drugs which prevent Ad induced inhibition of host cell protein synthesis can be added to cells used in the packaging system, thereby significantly slowing loss of viability and lysis of the packaging cell. The use of these drugs during the packaging process will result in a longer duration of expression of viral proteins required for packaging of recombinant Ad vectors. Such drugs include but are not limited to 2AP. Tyrosine kinase inhibitors such as genistein have similar effects, and can be used in accordance with the invention to improve packaging efficiency of the artificial genomes. FIG. 5 demonstrates that infected cells treated with 2AP show a significantly reduced cytopathic effect. Moreover, as presented in FIGS. 6 and 7, adenovirus induced loss of cell structural integrity and viability is promoted by viral disruption of the cytokeratin network, and inhibition of cell protein synthesis which are blocked to a large extent by treatment of cells with 2AP. Thus, by inhibiting either or both Ad degradation of cytokeratin K7/K18 and cell protein synthesis, the duration for replication of artificial genomic DNAs and synthesis of viral polypeptides required for formation of virion particles can be extended, resulting in greater trans-packaging before the packaging cells eventually die. Several approaches can be used to this end. Cells containing vectors for trans-packaging can be treated with agents such as 2AP or genistein to block CPE and viral shutoff of cell protein synthesis. Alternatively, cell lines have been described which are significantly resistant to Ad inhibition of host protein synthesis and CPE (e.g., Schneider et al. 1985; Huang and Schneider 1990). Use of these lines, or others that lack keratins K7/K18 will also extend the period during which trans-packaging can be carried out.

During infection of cultured cells with wild-type Ad only 5-10% of genomic viral DNAs and 10-20% of viral structural proteins actually proceed to mature infectious viral particles. The reasons for poor packaging and particle assembly are unknown, and no experimental data have been reported that provide a molecular explanation. However, several Ad structural polypeptides (e.g., L3-23kDa protease, proteins IIIa, V, IVa2, X-XII) that are critical for particle assembly are synthesized at low levels during infection, and may be limiting. Alternatively, packaging of empty Ad capsids may be coupled or temporarily linked to ongoing viral DNA replication, involving the threading of viral genomic DNA into preformed immature viral particles. In addition, since Ad particles form highly structured lattice-like arrays during infection, encapsidation of genomic DNAs into a significant fraction of particles may be sterically blocked.

Mutation of additional or other Ad functions besides the 23kDa protease activity can be incorporated into the helper system to promote more efficient production of trans-packaged artificial genomes. Polypeptides identified above, for instance, which are made at low levels, can be supplemented by placing their respective coding regions on plasmids under the control of strong promoters, and expressed in cells containing helper DNA by cotransfection. To better couple synthesis of artificial genomes and assembly of capsids, accumulation or activity of certain structural polypeptides can be provided in a regulated manner. For instance, protein IIIa can be deleted from the helper DNA, and its expression regulated from a separate plasmid or built into 293/T-Ag cells. Deprivation of protein IIIa blocks accumulation of young and mature particles. This approach is generally superior to the use of its mutants, many of which display reduced capsid stabilities even at permissive temperatures. Other proteins which can be utilized in a similar manner include but are not limited to those mentioned above. Deletion of respective structural or minor core polypeptides can be produced in the H5 to 1 genetic background, providing the ability to largely block assembly of viral particles but initiate assembly when high levels of artificial genomes are in the process of replication. The following criteria can be used for choosing Ad structural or core genes to be mutated and expressed independently in a regulated manner in the helper system. The gene product must be vital for formation of viral particles, such that its absence prevents accumulation of young or mature capsid particles, thereby permitting accumulation of particles capable of encapsidating genomes. The gene product must also be of low enough abundance in the viral particle that it can actually be quickly provided by an independent source to proper levels when desired.

5.3. Generation of Recombinant Virus Stocks

Another aspect of the invention relates to methods for replicating and packaging the artificial genomes into Ad particles that can non-productively infect cells. According to the method of the invention, recombinant adenovirus stocks may be produced by cotransfecting an appropriate cell type with the artificial genome and the helper Ad DNA. Prior to co-transfection, the artificial genome is restriction digested to free the ends of the ITRs permitting recognition by the Ad DNA replication apparatus. Cotransfection may be performed by the DEAE-dextran method (McCutchen and Pagano, 1968, J. Natl. Cancer Inst. 41:351-357), the calcium phosphate procedure (Graham et al., 1973, J. Virol. 33:739-748) or by any other method known in the art, including but not limited to microinjection, lipofection, and electroporation. Amounts of recombinant Ad vector and helper DNA used in transfections, are often from ~0.2 μg to 10 μg of DNA per $10^6$ cells, but vary among different DNA constructs and cell types. These ranges are not rigid. Cells suitable for transfection of recombinant vectors include any cell line permissive for Ad infection, including, but not limited to HeLa cells or human 293 cells (human embryonic kidney cells transformed with a fragment of Ad 5 DNA).

Cells are later harvested, typically from 3-10 days post-transfection. Routine procedures for lysis of cells are used such as repeated freeze-thaw or gentle sonication (Graham and Prevec, 1991, Methods Mol. Biol., 7:109-128). If a helper virus is used to provide capsid and replication proteins, it is separated from the Ad particles containing recombinant Ad DNA. Separation is achieved by first isolating the mixture of Ad virus particles in CsCl density step gradients (Graham and Prevec, 1991, Methods Mol. Biol., 7:109-128.). Particles are then subjected to continuous density isopyknic centrifugation in CsCl. Previous studies have shown that Ads differing by as little as 15% in genome length (e.g., 37.1 vs. 31.7 kb) can be effectively separated in this manner (Weinberger et al., 1987, UCLA Symp. Mol. Cell. Biol., Chalberg & Ketner, 1981). Additionally, heating the virus sample prior to gradient centrifugation has been shown to preferentially disrupt the Ad particles formed with oversized genomes in the absence of protein IX (Ghosh-Choudhury et al., 1987, EMBO J. 6:1733-1739). If helper function is provided by the use of the autonomously replicating Ad genomic plasmid devoid of ITRS, helper viruses are not produced since the Ad replication and packaging sequences are not present.

Corroboration of the resulting recombinant viral stock may be accomplished by the isolation of low-molecular weight DNA according to the method of Hirt (1967, J. Mol. Biol. 26:365-369), with subsequent evaluation for the presence of appropriate DNA sequences, using methods well known in the art.

In an alternative method related to that described above, artificial genomes are replicated with helper to produce stock artificial genomes with covalently attached terminal protein (pTP). Purification of the pTP-artificial genome stock can be achieved by lysing cells and isolating pTP-genomic DNAs using BND-cellulose chromatography as described (Hay et al. 1984, J. Mol. Biol. 175:493-510). Ad genomic DNAs with pTP already covalently attached are remarkably better templates for replication than DNAs devoid of protein, when tested in transfected cells (reviewed in Tamanoi & Stillman, 1983). Thus, by cotransfecting pTP-primed artificial genomic DNA and helper DNA, much higher levels of replication of genomic DNA is achievable compared to that obtained from vectors by restriction digestion. Other than initial generation of pTP-linked genomic DNA, the method for trans-packaging is practiced as described above.

5.4 Uses of Viral Vectors

The present invention relates to a novel adenovirus based trans-packaging system for replication and encapsidation of recombinant DNA into infectious adenovirus particles. The system involves the use of a recombinant viral vector which contains heterologous genes of interest and the minimum genomic adenovirus sequences required for replication and encapsidation of said vector DNA. The recombinant viral stocks of the present invention, which contain recombinant Ad DNA and a heterologous gene of interest may be useful for a variety of gene therapy applications including introduction, replacement, augmentation and regulation of genes in cells for treatment or correction of genetic disorders; for delivery of genes with anti-oncogenic, antiviral, antimicrobial or anti-mycotic activities to cells; for introduction and expression of genes in cells to elicit immune reactivity as a vaccine; for delivery of genes to cells expressing anti-sense or catalytic (e.g., ribozyme) RNAs; for introduction and expression of genes to cells to synthesize molecules that aid in diagnostics; to introduce into cells and express molecules that act as biological response modifiers; and to introduce into cells genes whose expression promote cell growth, replication and proper tissue development.

6. EXAMPLE

Inhibition of Virally Induced Shutoff of Host Protein Synthesis 6.1. Materials and Methods 6.1.1. Viruses, Cells, and Plasmids Ad 300 is a wild type strain 5 isolate (H5wl300) originally purified by H. Ginsberg is available through the ATCC. Ad2 ts1 is described in Chen et al., 1993, J. Virol. 67:3507-3514. 293 cells are human embryonic kidney cell line that express the E1 region of Ad5 (Graham et al., 1977, J. Gen. Virol. 36:59-72). 293 and HeLa cells were cultured in Dulbecco's modified Eagle's medium (DMEM) containing 10% calf serum. Virus stocks were grown and titers were determined on 293 cells. RD (human rhabdosarcoma) cells were obtained from the American Type Culture Collection and grown in DMEM containing 15% fetal bovine serum. 2AP was prepared and used as previously described (Huang & Schneider, 1990, PNAS USA 87:7115-7119). Infections of cells with viruses were typically carried out for 1 h with 50 PFU per cell unless otherwise noted.

6.1.2. Labeling of Cells and Analysis of Polypeptides

Cells were labeled with [$^{35}$S]methionine for 1 to 2 h by using 50 μCi of trans[$^{35}$S]methionine (ICN) per ml in DMEM lacking methionine and supplemented with 2% calf serum. Cell extracts were prepared by sonication of washed cells in 10 mM KCl-10 mM Tris (pH 7.4)–1 mM EDTA at 4° C. and cleared of debris by centrifugation at 10,000 rpm equal amounts of protein were analyzed in sodium dodecyl sulfate (SDS)-polyacrylamide gels. Gels were fluorographed and quantitated by densitometry.

6.1.3. Indirect Immunofluorescence Staining and Photography of Cells

Cells were grown on coverslips, fixed with paraformaldehyde, and permeabilized with Triton X-100. Mouse monoclonal antibodies directed against vimentin were purchased from Boehringer Mannheim Biochemicals. A mouse monoclonal antibody specific for keratins K18 (KS-B17.2) and K1, 5 to 8, 10, 11, and 18 (no. 8.13) were from Sigma Chemical Co. Fluorescein isothiocyanate-conjugated rabbit anti-mouse antibodies were purchased from Sigma. Cells were photographed under visible or ultraviolet light using a Zeiss photomicroscope.

6.2. Results 293 cells were treated with 2AP for the duration of infection, starting shortly after the addition of virus. Duplicate plates of cells were then labeled with [$^{35}$S]methionine, and extracts were analyzed by SDS-polyacrylamide gel electrophoresis (FIG. 7) or photographed at various times after infection for evidence of CPE (see FIG. 5). The ability of 2AP to prevent Ad shutoff of cell protein synthesis while maintaining high rates of translation for late Ad mRNAs was apparent (FIG. 7). Levels of cellular polypeptide synthesis (e.g., actin and background bands) as well as of Ad mRNAs which lack the tripartite leader (e.g., protein IX) were all significantly elevated by treatment of cells with 2AP.

Most striking was the large reduction in CPE in Ad-infected 293 cells treated with 2AP (FIG. 5). 293 cells are exquisitely sensitive to late Ad CPE as shown and generally displayed severe morphological alterations such as swelling, detachment from the monolayer, and lysis by 24 to 48 h after infection. Infected cells treated with 2AP demonstrated only slight CPE at 24 and 48 h. As observed with infected RD cells, by 48 h after infection some 2AP-treated 293 cells began to detach from the monolayer but there was little evidence that large numbers of cells lysed. Uninfected cells treated with 2AP did not demonstrate evidence of drug toxicity until -3 days after treatment. Similar effects of 2AP in Ad-induced CPE were also observed for infected KB and HeLa cells. These results, therefore, indicated that accumulation of abundant amounts of late Ad polypeptides was not particularly cytotoxic and was not likely to account for CPE during the late phase of infection.

Experiments were performed to test whether coupled shutoff of host protein synthesis and cleavage of cytokeratins truly correlates with development of CPE. Mutant Ad2 ts1 (temperature sensitive in the L3 proteinase) was exploited to uncouple the two effects because it cannot cleave cytokeratins K7 and K18 at the restrictive temperature (39.5°C.) but efficiently inhibits host cell protein synthesis. Cells were infected with Ad1 ts1 at permissive (32° C.) and restrictive (39.5° C.) temperatures. At the permissive temperature (32° C.) the Ad replication cycle is somewhat delayed and late phase is not fully developed until approximately 36 h post infection compared with that at 24 h at 37° C. Nevertheless, at 32° C., infection with Ad2 ts1 was indistinguishable from that of wild type Ad (FIG. 6), causing gross morphological alterations and degeneration of the cytokeratin network as observed earlier. At the restrictive temperature, however, there was a striking difference form wild type Ad-infected cells. Cells infected with Ad1 ts1 possessed only partial manifestations of CPE, including slight swelling and rounding of (FIGS. 6B and E). Interestingly, staining of keratin filaments revealed that the cables were largely intact but poorly resolved. Thus, slight degeneration of the intermediate filament network was evident in the absence of keratin cleavage, similar to that of 2AP-treated cells infected with wild type Ad. In cells infected with Ad1 ts1 at 39.5° C. and treated with 2AP, the keratin network was remarkably well preserved (FIGS. 6C and F), resembling that of uninfected cells rather than that of wild type Ad-infected cells treated with 2AP. Distinct keratin cables were clearly visible despite productive Ad infection, and cells appeared almost identical to uninfected controls. Accordingly, at 39.5° C., the Ad1 ts1-infected cells only detached form the monolayer quite late in the infection and lysed more poorly than cells infected at the permissive temperature for L3 proteinase activity.

7. EXAMPLE

Construction of Recombinant Ad Vectors and Helper DNAs 7.1. Materials and Methods Cell lines used in this work include 293 cells, a human embryonic kidney cell line transformed with Ad E1 sequences that express E1A and E1B products in trans but not protein IX. Other lines include 293/T-Ag cells, 293 cells transformed with SV40 T-Ag which permits replication of transfected SV40ori containing plasmids.

7.1.1. Construction of Recombinant Vectors

Plasmids pAd-ITR and pWE15-ITR-Bam (FIG. 1) were constructed as follows. The Ad2 left ITR was obtained by digestion of plasmid pNL3C (Lucito & Schneider, 1992, J. Virol. 66:983-991) with EcoRI (nt 1), ends repaired by treatment with Klenow fragment and ligated to AscI linkers. The DNA was then digested with SacII (nt 358), ends repaired with Klenow fragment and HindIII linkers ligated. DNAs were digested with AscI and HindIII to create sticky ends, and the 358 bp fragment of the left ITR purified by gel electrophoresis. The Ad5 right ITR was obtained from plasmid pAd5 XbaIC (Halbert et al., 1984, J. Virol. 56:250-257), which contains the 84.7 mu-100 mu fragment of Ad5 cloned in pBR322 (XbaI to EcoRI). DNA was digested with EcoRI, repaired with Klenow, then NotI linkers added in one case or AscI linkers in another. DNA was then digested with SmaI, HindIII linkers added, and DNAs digested with HindIII/NotI or HindIII/AscI, and the right end 580bp fragment purified by electrophoresis. Two different vectors were prepared to receive the left and right end fragments. In plasmid pML2d the EcoRI site was converted to an AscI ste, and the NruI site converted to a NotI site using fill-in reactions and ligation to linkers as described above. In cosmid pWE15, the polylinker NotI site was converted to an AscI site in a similar manner. Since AscI resembles more closely the sequence of the authentic Ad replication signal than NotI, it was felt that this site would be preferable, particularly for replication of large fragments. Plasmid pAd-ITR was constructed by a three-fragment ligation between the left Ad ITR fragment (AscI-HindIII), the right Ad ITR fragment (HindIII-NotI) and the pML2d vector fragment (AscI to NotI). Cosmid pWE15-ITR was constructed in an analogous manner using the Ad right ITR that contains AscI rather than NotI sites. Plasmid and cosmid DNAs were propagated in bacteria. A variant of cosmid pWE15-ITR was constructed containing a single BamHI site in place of the HindIII site that joins the two ITR fragments, since there are several HindIII sites in the cosmid itself. pWE15-ITR was subjected to partial HindIII digestion, linear fragments purified, repaired with Klenow fragment, BamHI linkers added, digested with BamHI and religated. Variants containing BamHI joining the two ITRs were identified and propagated to create plasmid pWE15-ITR-Bam.

Inserts for ligation into pWE15-ITR-Bam and pAd-ITR were obtained by digestion of *E. coli* or mouse high molecular weight genomic DNAs with HindIII/AscI/NotI or BamHI/AscI and electrophoresis of DNAs in agarose gels. Gel sections corresponding to approximately 10 kb, 15 kb, 20 kb, 25 kb, 30 kb and 35 kb were excised, DNAs electroeluted, ligated to vectors and screened for inserts using standard methods (Sambrook et al., 1989). Vectors containing inserts are reffered to as pWE15-ITR-(DNA size) and pAd-ITR (DNA size).

7.1.2. Construction of Recombinant Helper DNA

The following packaging-defective helper viruses with mutations in the packaging elements were utilized: virus Ad5 dl309-194/273 (packaging reduced 5-10 fold) and dl309-267/358 (reduced >50 fold) (Grable & Hearing, J. Virol. 64:2047-2056, 1990). Stocks were propagated in Hela cells to avoid recombination with Ad sequences present in 293 cells, analyzed by restriction digestion and titered by plaque assay before use.

Packaging defective helper virus Ad5 dl313-SV40 containing an Ad genome 104% the normal size was constructed as follows. Purified Ad5 dl313 DNA contains a deletion from bp 1334-3639 which eliminates expression of regions E1A, E1B and protein IX (Jones & Shenk, 1979, Cell 17:683-689) was digested with ClaI and the 2.3 map unit (mu) to 100 mu fragment purified on sucrose gradients as described (Graham & Prevec, 1991, Meth. of Mol. Biol. 7:109-128). SV40 DNA was digested at EcoRI and EcoRV, DNA repaired with Klenow fragment, SalI linkers added, digested with SalI and the 4.2 kb fragment purified by agarose gel electrophoresis using standard techniques (Sambrook et al., 1989). Plasmid pNL3C was described previously, (Lucito & Schneider, 1992). Briefly, it consists of the 1-350 bp fragment of Ad2 containing the ITR-packaging and replication signals, the Ad2 major late promoter and cDNA of the tripartite leader 5' noncoding region, region E1A and E1B in the background of pBR322 variant pML2d. Plasmid pNL3C was digested with SalI and ligated to the SV40 SalI fragment, colonies screened and positive transformants obtained (pNL3C-SV40). Plasmid pNL3C-SV40 was linearized at NruI, and 2 ug coprecipitated onto 293 cells with 5 ug of the 2.3-100 mu fragment of dl313 using the calcium phosphate precipitation technique. Overlap recombination gave rise to small plaques containing the oversized (104%) genome, which were identified and propagated as described previously (Graham & Prevec, 1991). All viral stocks were plaque purified, analyzed by restriction enzyme digestion and titered before use.

Construction of complementing cosmid for adenovirus gene functions (pWE15-ts1) was carried out as follows (FIG. 3). Purified, protease treated genomic DNA was prepared from Ad5ts1 and Ad5 dl309 as described (Graham and Prevec, 1991). Ad5 ts1 DNA was digested with ClaI (2.5mu) and EcoRI (which preferentially cuts the 83.5mu rather than the 76mu site), repaired with Klenow fragment, BscI linkers added, digested with BscI and the large 2.5mu-83.5mu fragment purified by sucrose gradient centrifugation as described above. Ad5 dl309 DNA was digested with SnaBI (¯99.6mu), repaired with Klenow, BscI linkers added and digested as just described, then digested with EcoRI and the 5.7kb fragment purified by gel electrophoresis. Cosmid pWE15-ts1 was then constructed by a three fragment ligation between BscI linearized vector, the BscI/EcoRI 2.5-83.5mu ts 1DNA and EcoRI/BscI Ad5dl309 DNA. Cosmids the containing correct fragments were identified by restriction digestion analysis and propagated in bacteria.

7.1.3. Trans-Packaging of Artificial Genomes Using Helper Virus

Several different approaches can be used to provide complementing activities for trans-packaging of artificial genomes. The approach described here utilizes either of two complementing Ad viruses. Full-length genomic viral DNA was purified from cells infected with either Ad5 dl309-194/273, dl309-267/358 or dl313-SV40 utilizing protease treatment to remove pTP from the DNA terminii as described (Graham & Prevec, 1991). Artificial genomic DNAs were liberated from cosmid and plasmid vectors by digestion with AscI or AscI/NotI, respectively. Typically, 2-5 µg of helper virus DNA was cotransfected with an equivalent amount of artificial genomic DNA onto 10cm plates of 293 cells at 50% confluency using the calcium phosphate coprecipitation technique. Cells were then harvested at various times following transfection, typically between 3-10 days. To largely prevent facilitated cell lysis due to adenoviral late gene activity, cells can be treated with 10 mM 2AP or 50-100 µM genistein shortly after transfection. Cells were lysed in 0.1 M TrisHCl pH 7.5 by gentle sonication or repeated freeze-thaw and debris removed by centrifugation at 10,000×g for 5 minutes. Virus particles were then purified by density centrifugation in CsCl using a two-step gradient consisting of 1.25 gm/cc and 1.45 gm/cc CsCl. Virus particles were extracted from the interface, which served to remove most debris and unencapsulated empty particles and light intermediates. In the case of complementation by the Ad dl313-SV40 virus, particles were heated to 48° C. for 5 minutes, which results in a 1000 fold decrease in stability of full-length and oversized genomes. Particles were then further purified by isopyknic density centrifugation in CsCl as described (Graham & Prevec, 1991). Lighter particles containing shorter than genome-length articifical genomes can be separated from full-length or oversized remnant helper virus particles in this fashion.

7.1.4. Trans-Packaging of Artificial Genomes Using Cosmid Helper DNAs

Significantly increased replication of artificial genomes can be obtained if cells are transfected with artificial genomic DNAs covalently attached to pTP. This is particularly true when complementation and trans-packaging is carried out using cosmid pWE15-ts1. Large amounts of pTP-artificial genomes were obtained as follows. 293/T-Ag cells were cotransfected with approximately 5ug of undigested helper cosmid pWE15-ts1 and 2-5 µg artificial genome prepared by restriction enzyme digestion as described above (Section 7.1.3) into 293/T-Ag cells using calcium phosphate coprecipitation. After 3-5 days post-transfection, cells maintained at 39.5° C. were lysed and low molecular DNAs purified by the Hirt extraction procedure (Sambrook et al., 1989), but without protease digestion. DNAs are then chromatographed on benzoylated-napthalated-DEAE (BND)-cellulose and pTP-genomic DNAs eluted in 8 M urea and 1% SDS as described (Hay et al., J. Mol. Biol. 1984, 175:493-510). pTP-artificial genomes were then diluted, ethanol precipitated and resuspended in 10 mM TrisHCl pH7.5. pTP-DNAs corresponding to all size classes of artificial genomes described earlier were obtained at between 5-15% the level of replication of wild-type Ad genomes. Several lines of evidence were obtained indicating the authenticity of pTP covalent linkage to, and replication of artificial genomes: (1) amplification of input artificial genomic DNA, as detected by Southern blot analysis; (2)

elution of artificial genomic DNA from BND-cellulose in 8 M urea, which is specific for pTP-DNA complexes; and (3) retarded migration of non-protease digested artificial genomic DNA by agarose gel electrophoresis compared to protease-treated samples.

Trans-packaging of artificial genomes was carried out by typically cotransfecting 293/T-Ag cells with 1-3 μg of pTP artificial genome DNA, or 2-5 μg non-pTP DNA, with 2-5 μg non-digested helper cosmid pWE15-ts1. Cells were maintained at 39.5° C. to prevent activity of the L3-23kDa protease. Between 3-5 days post-transfection cells were shifted to 32° C. to provide L3-23kDa protease activity. Any of several drugs may be added to cells shortly after transfection to largely block CPE associated with L3-23kDa activity, including 2AP as described (Huang & Schneider, 1990, PNAS USA 87:7115-7119). Cells were maintained under these conditions for several additional days, then lysed and virus particles purified as described in Section 7.1.3. Use of helper (cosmid pWE15ts1 elminates the need to remove contaminating Ad particles containing helper viral genomes.

The present invention is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed:

1. A method for producing stocks of packaged artificial genomes, comprising:
    a) culturing a packaging host cell containing an artificial genome having elements that function as adenovirus replication and packaging signals flanking an intervening fragment of DNA, in which the packaging host cell provides the viral functions encoded by a helper adenovirus genomic DNA with impaired ITR function, which cannot be packaged into infectious virions and is larger than adenovirus genome length, and wherein the viral functions are sufficient for the replication and packaging of the artificial genome into infectious virions; and
    b) collecting the virions produced by the cultured packaging host cell.

2. The method of claim 1 in which the elements of the artificial genome are the ITR structures of adenovirus.

3. The method of claim 1 in which the intervening DNA fragment of the artificial genome lacks adenovirus coding sequences.

4. The method of claim 1 in which the helper adenovirus genomic DNA contains a mutant packaging element wherein the helper adenovirus genomic DNA cannot be packaged into infectious virions.

5. The method of claim 1 in which the adenovirus genomic DNA lacks ITR function and is contained in a DNA vector.

6. The method of claim 1 in which the cultured packaging cells are treated with 2-aminopurine.

7. The method of claim 1 in which the cultured packaging cells are treated with genistein.

8. The method of claim 1, wherein the artificial genome contains unique restriction endonuclease sites externally flanking the elements.

9. The method of claim 1, wherein the artificial genome ranges from about 10 kb to about 35 kb.

10. The method of claim 5 in which the helper DNA vector is a plasmid or a cosmid.

11. The method of claim 5 in which the DNA vector autonomously replicates.

12. The method of claim 1, 4, 5, 10 or 11 in which the helper adenovirus DNA contains a temperature sensitive mutation in the L3-23kDa viral protease, wherein the L3-23kDa viral protease is inactive at the restriction temperature but not at the permissive temperature.

13. A helper adenovirus genomic DNA with impaired ITR function encoding adenoviral functions sufficient for replication and packaging of an artificial genome, in which the helper adenovirus genomic DNA is larger than the adenovirus genome length.

14. A helper adenovirus genomic DNA which lacks ITR function and encodes adenoviral functions sufficient for replication and packaging of an artificial genome, contained in a DNA vector.

15. The helper adenovirus genomic DNA of claim 14 in which the DNA vector is a plasmid or a cosmid.

16. The helper adenovirus genomic DNA of claim 14 in which the DNA vector autonomously replicates.

17. The helper adenovirus genomic DNA of claim 13, 14, 15, or 16 which contains a temperature sensitive mutation in the L3-23kDa viral protease wherein the L3-23kDa viral protease is inactive at the restrictive temperature but not at the permissive temperature.

* * * * *